(12) United States Patent
Laskey (10) Patent No.: US 10,267,801 B2
(45) Date of Patent: Apr. 23, 2019

(54) ASSAY

(71) Applicant: Cytosystems Limited, Aberdeen (GB)

(72) Inventor: Ronald Alfred Laskey, Cambridge (GB)

( * ) Notice: Subject to any disclaimer, the term of this patent is extended or adjusted under 35 U.S.C. 154(b) by 449 days.

(21) Appl. No.: 14/489,207

(22) Filed: Sep. 17, 2014

(65) Prior Publication Data
US 2015/0219659 A1 Aug. 6, 2015

Related U.S. Application Data

(63) Continuation of application No. 13/512,823, filed as application No. PCT/GB2010/002274 on Dec. 15, 2010, now abandoned.

(30) Foreign Application Priority Data

Dec. 15, 2009 (GB) .................................. 0921873.6

(51) Int. Cl.
*G01N 33/68* (2006.01)
*G01N 33/574* (2006.01)

(52) U.S. Cl.
CPC ... *G01N 33/57434* (2013.01); *G01N 33/6893* (2013.01); *G01N 2333/723* (2013.01)

(58) Field of Classification Search
None
See application file for complete search history.

(56) References Cited

U.S. PATENT DOCUMENTS

| | | | |
|---|---|---|---|
| 6,258,540 B1 * | 7/2001 | Lo .................. | C12Q 1/6879 435/440 |
| 6,303,323 B1 | 10/2001 | Laskey et al. | |
| 6,355,623 B2 * | 3/2002 | Seidman .............. | A61K 31/52 514/263.4 |
| 6,566,130 B1 | 5/2003 | Srivastava et al. | |
| 7,056,690 B2 | 6/2006 | Laskey et al. | |
| 7,459,157 B2 | 12/2008 | Laskey et al. | |
| 2003/0105000 A1 | 6/2003 | Pero et al. | |
| 2005/0079576 A1 | 4/2005 | French et al. | |
| 2006/0211059 A1 | 9/2006 | Taneja | |
| 2007/0105105 A1 | 5/2007 | Clelland et al. | |
| 2011/0184073 A1 | 7/2011 | Galloway | |

FOREIGN PATENT DOCUMENTS

| | | |
|---|---|---|
| WO | WO 2006/091776 A2 | 8/2006 |
| WO | WO 2009/050461 A1 | 4/2009 |

OTHER PUBLICATIONS

Boyd, N. F., The Basic Scinece of Oncology, 1992 McGraw-Hill, Inc., p. 379.
Burgess, W.H. et al., "Possible Dissociation of the Heparin-Binding and Mitogenic Activites of Heparin-Binding (Acidic Fibroblast) Growth Factor-1 from its Receptor-Binding Activites by Site-Directed Mutagenesis of a Single Lysine Residue", J. of Cell Bio., vol. 111, p. 2129-2138, 1990.
Coleman, P.M., "Effectsof Amino Acid Sequence Changtes on Antibody-Antigen Interactions", (Research in Immunology, 1994; 145(1): 33-36.
Diallo, J-S, et al. "Co-Assessment of Cytoplasmic and Nuclear Androgen Receptor Location in Prostate Specimens: Potential Iplications for Prostae Cancer Development and Prognosis", Investigative Urology, vol. 101, p. 1302-1309, Feb. 2008.
MeSH-MCIV17 protein, human NCBI Nov. 1, 1996.
Fujita, K., et al., "Specific Detection of Prostate Cancer Cells in Urine by Multiplex Immunofluorescence Cytology," v. 40, n. 7, p. 924-933, Jul. 1, 2009.
Levesque, M-H, et al., "Evaluation of AlbZIP and Cdc47 as Markers for Human Prostatic Diseases," Urology, v. 69, n. 1, p. 196-201, Jul. 2007.
Matsushita et al. "The Latrophilin Family: Multiply Spliced G Protein-Couple Receptors with Differential Tissue Distribution", FEBS Letters, vol. 443, pp. 348-352, 1999.
Meng, M.V., et al., "Minichromosome Maintenance Prtotein 2 Expression in Prostate: Characterization and Association with Outcome After Therapy for Cancer," Clin. Cancer Res., v. 7, n. 9, p. 2712-2718, Sep. 1, 2001.
Nariculam, J. et al., MCM-2 Expression in Clinically Localised Prostate Cancer, Euro. Urology, v. 7, n. 3, p. 255, Feb. 20, 2008.
Nariculam, J. et al., MCM-2 Expression in Clinically Localised Prostate Cancer, Euro. Urology Suppl, v. 7, n. 3, p. 255, Mar. 1, 2008.
Padmanabhan, V. et al., "DNA Replication Regulation Protein Mcm7 as a Marker of Proliferation in rostate cancer," J. of Clinical Path., v. 57, n. 10, p. 1057-1062, Oct. 1, 2004.
Pritzker, "Cancer Biomarkers: Easier Said than Done", Clinical Chemistry, 2002, v. 48, No. 8, p. 1147-1150, (2002).
Ren, B., et al., "MCM7 Amplification and overexpression are Associated with Prostate Cancer Progression," Oncogene, v. 25, n. 7, p. 1090-1098, Feb. 1, 2006.
Rudikoff, S. et al., "Single Amino Acid Substitution Altering Antigen-binding Specificity", (PNAS, vol. 79, p. 1979-1983, Mar. 1982.
Saramaki, Outi., et al., "Chromosomal Aberrations in Prostate Cancer," Frontiers in Bioscience, v. 12, p. 3287-3301, May 1, 2007.
Shi, Y-K, et al., "MCM7 Interacts with Androgen Receptor", Amer. J. Pathol., vol. 173, No. 6, Dec. 2008.
Simon, R.A., et al., "Minichromosome Maintenance Protein 6 Expression in the Prostate: A Tissue Microarray Analysis", Accession No. 2006:366644 Biosis, Lab. Invest., vol. 86, No. 51, pp. 161A, Abs. 746, Jan. 2006.
Singh, R. et al., "Cell-Surface-Expressed Thomsen-Friedenreich Antigen in Colon Cancer is Predominantly Carried on High Molecular Weight Splice Variants of CD44", Glyocbiology, vol. 11, No. 7, pp. 587-592, 2001.
Stoeber, K., et al., "Diagnosis of Genito-Urinary Tract Cancer bydetection of Minichromosome maintenance 5 Protein in Urine Sediments," J. Natl Cancer Inst., v. 94, n. 14, p. 1071-1079,Jul. 17, 2002.
Watkins et al., (Proc. Amer. Assoc. Cancer Res., 96th Annual Meeting, Apr. 16-20, 2005, Abstract #3163).

* cited by examiner

*Primary Examiner* — Peter J Reddig
(74) *Attorney, Agent, or Firm* — Gary Baker; BioPatent (57) ABSTRACT

This disclosure relates to a diagnostic/prognostic assay for prostate cancer and including kits used in said assay.

16 Claims, 9 Drawing Sheets

Figure 2 a) AR-N20 DAB b) AR-C19 DAB c) PSA DAB d) MCM2 Nova red e) MCM7 Nova red

Figure 3
PSA DAB-Ni, MCM2 red

ASSAY

CROSS-REFERENCE TO RELATED APPLICATIONS

The present application is a of continuation of U.S. Ser. No. 13/512,813, filed Aug. 9, 2012, now abandoned, which is a national phase application of PCT Application No. PCT/GB2010/002274 filed Dec. 15, 2010, which claims priority to GB application no. 0921873.6, filed on Dec. 15, 2009. PCT Application No. PCT/GB2010/002274 and GB application no. 0921873.6 are incorporated herein by reference in its entirety for all purposes.

FIELD OF THE INVENTION

The invention relates to a diagnostic/prognostic assay for prostate cancer and including kits used in said assay.

BACKGROUND OF THE INVENTION

Cancer is an abnormal disease state in which uncontrolled proliferation of one or more cell populations interferes with normal biological function. The proliferative changes are usually accompanied by other changes in cellular properties, including reversion to a less organised state. Cancer cells are typically referred to as "transformed". Transformed cells generally display several of the following properties: spherical morphology, expression of foetal antigens, growth-factor independence, lack of contact inhibition, anchorage-independence, and growth to high density. Cancer cells form tumours and are referred to as "primary" or "secondary" tumours. A primary tumour results in cancer cell growth in an organ in which the original transformed cell develops. A secondary tumour results from the escape of a cancer cell from a primary tumour and the establishment of a secondary tumour in another organ. The process is referred to as metastasis and this process may be aggressive, for example as in the case of hepatoma or lung cancer. Prostate cancer can be relatively harmless or extremely aggressive. Some prostate tumours are slow growing and cause few clinical symptoms. Aggressive prostate tumours spread rapidly to the lymph nodes and other organs, especially bone. It is known that the growth of prostate cancer can be inhibited by blocking the supply of male hormones such as testosterone. However, prostate cancers eventually develop and become independent of male sex hormones (i.e. they become androgen-independent prostate cancer cells). These cells are linked with aggressive, malignant prostate cancer. Only two species suffer from prostate cancer; dogs and humans.

Previous studies have identified minichromosome maintenance proteins (MCM) as key regulators in the cell cycling process of epithelial tissue (see WO99/21014 and Gonzalez et al; Nature Reviews/Cancer, Vol 5: pp 135-141, February 2005). MCMs were identified as useful biomarkers of "cell cycle state", i.e. whether a cell is capable of proliferating rather than being quiescent or senescent. Expression of all 6 MCMs (MCM 2-7) is seen throughout all phases of the cell cycle and is down regulated following exit from the cell cycle into quiescence, differentiation or senescence. Androgen Receptor [AR] is a nuclear protein that binds the androgens testosterone and dihydrotestosterone. AR is a transcription factor and is involved controlling genes involved male sex determination. The cloning and sequencing of AR is disclosed in WO89/09791 which describes the expression of AR in prokaryotic and eukaryotic expression systems and its use in the development of monoclonal antibodies. The detection of PSA as a diagnostic test to detect prostate cancer is well established. PSA is a protease secreted by the cells of the prostate gland. The detection of PSA in a blood sample is considered to be indicative of prostate cancer in a subject. This has considerable problems associated with clearly identifying whether a subject requires further investigation. Some subjects that present with high serum levels of PSA are eventually found not to have disease. This causes both psychological stress and unnecessary physical investigation.

We disclose an assay that provides a reliable test for the detection of prostate cancer cells in an isolated cell sample from a biological sample and removes the current problems associated with the detection of prostate specific antigen in serum samples of male subjects.

SUMMARY OF THE INVENTION

In one aspect of the invention, it is provided a diagnostic or prognostic assay for the detection of prostate cancer cells in a biological sample. In some embodiments, the diagnostic or prognostic assay includes: i) obtaining an isolated cell sample from said biological sample and contacting the isolated cell sample with a binding agent that specifically binds a MCM polypeptide; ii) contacting the isolated cell sample with a further binding agent that specifically binds an androgen receptor polypeptide [AR]; optionally iii) contacting the isolated cell sample with a still further binding agent that specifically binds prostate specific antigen [PSA]; iv) detecting the binding of two or more binding agents; and v) determining the number of cells in said isolated cell sample that positively bind two or more binding agents, wherein the number of positive cells is an indicator of the presence of prostate cancer cells in the biological sample.

In another aspect of the invention, it is provided a diagnostic or prognostic assay for the determination of prostate cancer in a subject. In some embodiments, the diagnostic or prognostic assay includes i) obtaining a first isolated biological sample and contacting the sample with a binding agent that specifically binds PSA; optionally ii) detecting the presence of PSA in said sample; iii) obtaining a second biological sample from the subject, preparing an isolated cell sample and contacting said cell sample with first and second binding agents that specifically bind a MCM polypeptide and an androgen receptor polypeptide; iv) detecting the presence of said MCM polypeptide[s] and androgen receptor; and v) determining the number of cells in said isolated cell sample that positively bind both MCM and androgen receptor, wherein the number of positive cells is an indicator of the presence of prostate cancer cells.

DESCRIPTION OF THE DRAWINGS

An embodiment of the invention will now be described by example only and with reference to the following figures.

DETAILED DESCRIPTION OF THE INVENTION

According to an aspect of the invention there is provided a diagnostic or prognostic method for the detection of prostate cancer cells in a biological sample comprising the steps:
i) obtaining an isolated cell sample from said biological sample and contacting the isolated cell sample with a binding agent that specifically binds at least one MCM polypeptide;
ii) contacting the isolated cell sample with a further binding agent that specifically binds a nuclear receptor polypeptide; optionally
iii) contacting the isolated cell sample with a still further binding agent that specifically binds prostate specific antigen [PSA];
iv) detecting the binding of two or more binding agents; and
v) determining the number of cells in said isolated cell sample that positively bind two or more binding agents, wherein the number of positive cells is an indicator of the presence of prostate cancer cells in the biological sample.

In a preferred assay of the invention said nuclear receptor polypeptide is Androgen receptor polypeptide (AR).

In a preferred assay of the invention said MCM polypeptide is selected from the group consisting of: MCM2, MCM3, MCM4, MCM5, MCM6 or an MCM7 polypeptide.

In a preferred assay of the invention said MCM polypeptide is MCM2 and/or MCM7.

In a preferred assay of the invention said MCM polypeptide is MCM2.

In an alternative preferred assay of the invention said MCM polypeptide is MCM7.

In a further preferred assay of the invention said MCM polypeptide is MCM2 and MCM7.

In preferred assay of the invention said cell sample is contacted with a binding agent that specifically binds AR and a binding agent that specifically binds PSA.

In a preferred assay of the invention said assay detects at least one MCM polypeptide, AR and PSA.

In a preferred assay of the invention said assay detects MCM2 and/or MCM7, AR and PSA.

In a preferred assay of the invention steps (ii) and (iii) are reversed.

In a preferred assay of the invention said binding agent is a monoclonal antibody, or active binding fragment thereof.

It will be apparent that the assay provides a diagnostic tool to determine whether a subject has or has not a predisposition to prostate cancer. It also provides a means to determine whether a subject diagnosed and undergoing therapy, for example chemotherapy or radiotherapy, is responding to the treatment or requires and additional or alternative treatment regime. The invention therefore provides a treatment regime for a subject to better manage his disease.

In a preferred method of the invention said biological sample is a sample of isolated bodily fluid, for example urine, semen or seminal fluid.

Biological samples are typically rapidly processed to reduce degradation of the sample and provide a reliable measure of expression of selected markers. For example samples are chilled [e.g. 4° C.] and processed within at least 1 hour of being obtained.

In a preferred assay of the invention said biological sample is a filtered wherein said filtered sample provides said isolated cell sample.

An example of a filtration device useful in the operation of the invention is disclosed by the applicant in WO2009/087375, which is incorporated by reference. The filtration device comprises a filter adapted to collect cells of a predetermined size; a fluid pathway arranged to transmit fluid to and from the filter; and a pump which provides a positive pressure which urges the fluid to the filter along the fluid pathway and a negative pressure which draws the fluid from the filter along the fluid pathway.

According to a further aspect of the invention there is provided a diagnostic or prognostic assay for the determination of prostate cancer in a subject comprising the steps:
i) obtaining a first isolated biological sample and contacting the sample with a binding agent that specifically binds PSA; optionally
ii) detecting the presence of PSA in said sample;
iii) obtaining a second biological sample from the subject, preparing an isolated cell sample and contacting said cell sample with first and second binding agents that specifically bind at least one MCM polypeptide and an androgen receptor polypeptide;
iv) detecting the presence of said MCM polypeptide[s] and androgen receptor; and v) determining the number of cells in said isolated cell sample that positively bind both MCM and androgen receptor, wherein the number of positive cells is an indicator of the presence of prostate cancer cells.

In a preferred assay of the invention said first biological sample comprises serum.

In a further preferred assay of the invention said second biological sample is urine or semen.

In a preferred assay of the invention said MCM polypeptide is MCM2 and/or MCM7.

In a preferred assay of the invention said MCM polypeptide is MCM2.

In an alternative preferred assay of the invention said MCM polypeptide is MCM7.

In a preferred assay of the invention said detection of binding agents is by fluorescence emission.

In an alternative preferred assay of the invention said detection of binding agents is by enzymic means.

The binding of a specific binding agent such as an antibody on normal and test samples may be determined by any appropriate means. Labels include fluorochromes, phosphor or laser dye with spectrally isolated absorption or emission characteristics. Suitable fluorochromes include fluorescein, rhodamine, phycoerythrin and Texas Red.

Suitable chromogenic dyes include diaminobenzidine. Other labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. In the examples described below, alkaline phophatase or horseradish peroxidise have been employed.

According to a further aspect of the invention there is provided a kit comprising first second and third binding agents wherein said agents bind a MCM polypeptide, androgen receptor polypeptide and prostate specific antigen polypeptides respectively, In a preferred embodiment of the invention said binding agents are monoclonal antibodies.

In a further preferred embodiment of the invention said kit further comprises secondary antibodies that bind said first second and third monoclonal antibodies wherein each of said secondary antibodies are provided with fluorescence labels that facilitate the detection of said polypeptides.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Definitions

As used herein, a "binding agent" is an agent of a pair of molecules which have binding specificity for one another. The members of a specific binding pair may be naturally derived or wholly or partially synthetically produced. One member of the pair of molecules has an area on its surface, which may be a protrusion or cavity, which specifically binds to and is therefore complementary to a particular spatial and polar organisation of the other member of the pair of molecules. Thus, the members of the pair have the property of binding specifically to each other.

Examples of types of specific binding agent pairs are antigen-antibody, biotin-avidin, hormone-hormone receptor, receptor-ligand, enzyme-substrate, DNA-DNA (e.g. oligonucleotide). The present invention is generally concerned with antigen-antibody type reactions, although it also concerns small molecules which bind to the antigen defined herein.

The term "antibody" as used herein refers to immunoglobulin molecules and immunologically active portions of immunoglobulin molecules, i. e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e. g., IgG, IgE, IgM, IgD and IgA) and their isotypic subclasses; fragments which comprise an antigen binding domain such as Fab, scFv, Fv, dAb, Fd; and bivalent. Antibodies may be polyclonal or monoclonal.

As antibodies can be modified in a number of ways, the term "antibody" should be construed as covering any specific binding agent or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic.

Antibodies which are specific for a target of interest, such as MCM or AR or PSA, may be obtained using techniques which are standard in the art. Methods of producing antibodies include immunising a mammal (e.g. mouse, rat, rabbit) with the protein or a fragment thereof or a cell or virus which expresses the protein or fragment. Antibodies may be obtained from immunised animals using any of a variety of techniques known in the art, and screened, for example using binding of antibody to antigen of interest.

An antigen binding domain is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region.

"Specific" is generally used to refer to the situation in which one member of a specific binding pair will not show any significant binding to molecules other than its specific binding partner(s), e. g., has less than about 30%, preferably 20%, 10%, or 1% cross-reactivity with any other molecule.

The specific binding agents of the invention will preferably be, in accordance with the present invention, in "isolated" form. Members will generally be free or substantially free of material with which they are naturally associated such as other polypeptides with which they are found in their natural environment, or the environment in which they are prepared (e. g. cell culture) when such preparation is by recombinant DNA technology practised in vitro or in vivo.

Thus the specific binding agent of the invention is preferably an antibody, or fragment thereof. Thus, for example the specific binding agent may be an antibody, or fragment thereof, having an antigen binding domain specific for PSA or AR. For example, the specific binding agent may be an antibody, or fragment thereof, having an antigen binding domain specific for MCM e.g. MCM2 or MCM7. The antibody may be a polyclonal antibody, monoclonal antibody, single chain antibody or fragment of any of the foregoing. Preferably the specific binding agent is a monoclonal antibody. Monoclonal antibodies specific for MCM, AR and PSA are known in the art.

EXAMPLES

Examples are provided below to illustrate the present invention. These examples are not meant to constrain the present invention to any particular application or theory of operation.

Example 1

Colourimetric labelling of cultured prostate cancer cells with DAKO double-stain kit against PSA and MCM antigens.

C4-2b cells were cultured in T75 flasks in RPMI media containing 10% FBS and 2% penstrep at 37° C. and 5% $CO_2$ to 90% confluence. The media was removed by pipetting, and the cells were washed twice with warmed PBS. They were detached from the flask surface by incubating for 2-3 min in 10 ml trypsin solution at 37° C., followed by gentle agitation. The cell suspension was transferred to a 50 ml falcon tube, and the number of cells present determined by counting a sample on a haemocytometer. They were then pelleted by centrifugation and resuspended in warm PBS to $1 \times 10^6$ cells/ml. Aliquots of 150 µl were added to vials containing 20 ml of PreservCyt solution and transferred to the Thinprep-T2000 processor. This gently breaks up any cell debris, and provides a uniform suspension of cells. The suspension was drawn through a filter which collects a uniform layer of cells. By monitoring the resistance to flow, the instrument prevents collection of layers containing too few or too many cells. The entrapped cells were transferred to a UroCyte glass slide in a 10 mm diameter circle. The slide was then immersed in spirit (Cell Path Ltd. EGK-019500A), drained, and sprayed once with Surgipath coating fixative solution from a distance of 10 cm and placed on a flat surface to air dry.

Cell staining:—Cells were stained using a DAKO G/2 Double-stain kit (K5631) as follows:

Slides were immersed in 50% methanol for 5 min, and rinsed in distilled water before rinsing in TBS (Tris-HCl-buffered saline, DAKO reagent) They were then rinsed with distilled water followed by DAKO wash buffer (S3006), and transferred to the Autostainer (DAKO). Slides were blocked with 200 µl DAKO dual endogenous enzyme block (product code (K5361) for 5 min, then rinsed twice with TBS. Two hundred µl primary antibody A0562 rabbit anti-human PSA polyclonal antibody (or control rabbit antibody) was applied at 0.3 µg/ml and incubated for 30 min. All incubation steps were carried out at room temperature unless otherwise stated. Slides were rinsed twice with TBS, and 200 µl Envision (anti-rabbit) Polymer Horse Radish Peroxidase (HRP) conjugate (DAKO K5361) added and incubated for 30 min. Slides were rinsed twice again with TBS, DAKO DAB substrate was applied and slides incubated for 5 min. Slides were removed from the auto-stainer and rinsed in tap water for 3 min.

A heat retrieval step was performed next in order to make the MCM antigen accessible to antibody:—

Slides were immersed 1 mM EDTA heat retrieval buffer, pH7.8 (DAKO) and micro-waved on full power (800 W, 10 min.). Heat retrieval buffer was replenished, and microwaving repeated for 10 min. Slides were prepared in this way in batches of 10. Where a smaller number of samples were being prepared, blank slides were included to bring the total number to 10 for consistency of heat treatment. Slides were allowed to cool for 5 min and returned to the auto-stainer.

Slides were blocked again for 3 min with DAKO double-stain block (auxiliary reagent) and rinsed twice with TBS buffer. The $2^{nd}$ primary antibody, mouse anti-MCM2 D1.12A3 (MRC, Cambridge, UK) or control mouse antibody was added (200 µl at 1 µg/ml) and incubated for 60 min. Slides were rinsed twice with TBS, and Envision Polymer-alkaline phosphatase conjugate (DAKO K5361) added (200 µl) for 15 min. After two further rinses with TBS, 200 µl liquid permanent red alk-phos substrate (vol, DAKA code) was added for 7 min. This reagent was prepared freshly and added to the autostainer 30 min before use. It was supplemented with 1 drop/ml of DAKO X3021 levamisole (DAKO X3021) to block endogenous alk-phos activity.

After staining, slides were rinsed with distilled water and immersed in $CuSO_4$ solution (10 g $CuSO_4$, 17 g NaCl in 2 L water) for 5 min, then rinsed again with water. They were then counterstained with Haematoxylin for 10 s and rinsed with water. Finally slides were immersed in xylene for 5 min, air dried and cover-slipped ready for analysis.

Figure 1:
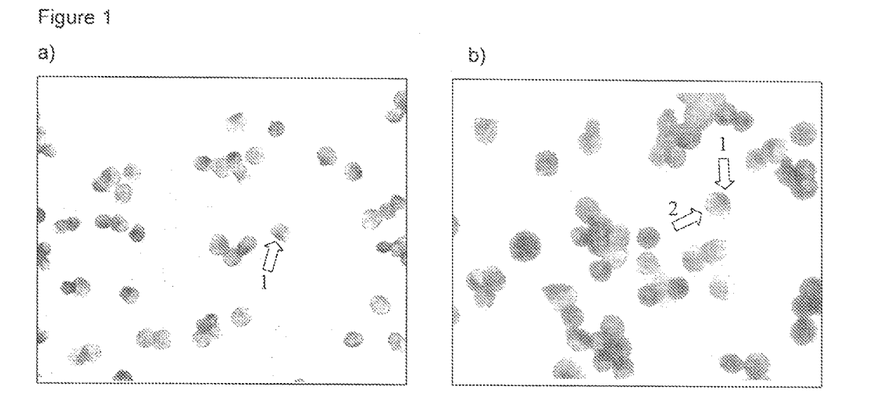
FIG. 1: DAKO colourimetric staining of cultured C4-2b prostate cancer cell line a) with anti-PSA (cytoplasmic), b). with anti-PSA (cytoplasmic) and anti-MCM2 (nuclear). Plate a) shows that anti-PSA antibody labels prostate cell cytoplasm (1), and that the nucleus is greatly enlarged (haematoxylin stain). Plate b) shows dual staining of cell cytoplasm with anti-PSA (1) and nucleus with anti-MCM2 antibodies (2).

Antibodies were diluted from stock solutions in DAKO antibody diluent (S0809 or S2022) to desired concentration. Slides were visualised under white light using a Zeiss AxioSKOP 40 microscope fitted with a Prog Res C14 colour camera. In addition to white light visualisation, the alkaline phosphatase substrate used to label MCM antigens emits fluorescence. This was observed using a Zeiss-Imager M2 with black and white camera Axiocam MRm and a red filter. Images were analysed with Axiovision software (FIG. 1).

In alternative assay formats, the DAKO rabbit anti-PSA polyclonal antibody A0562 at 0.3 µg/ml was substituted with one of the following:
i) Insight Biotechnology N-20 rabbit anti-androgen receptor N-terminus specific polyclonal antibody (sc816) at 0.3 µg/ml.
ii) Genetex anti-PSGR antibody (GTX72749) at 1/50 dilution
iii) Abcam mouse monoclonal anti-PSA epitope 3 antibody PS2 (ab10189) at 0.3 µg/ml.
iv) Abcam mouse monoclonal anti-PSA epitope 4 antibody 5G6 (ab10186) at 0.3 µg/ml.
v) Abcam rabbit anti-PSA polyclonal antibody (ab9537) at 0.3 µg/ml.

In addition, the D1.12A3 mouse anti-human MCM2 monoclonal antibody at 1.0 µg/ml was replaced with one of the following:
i) Santacruz 141.2 mouse anti-MCM7 monoclonal antibody sc-9966 at 3.0 µg/ml. (Antibodies raised specifically to either the N-terminus or C-terminus label MCM7 in the cytoplasm rather than the nucleus, and are therefore only suitable for use in conjunction with anti-AR antibodies in colourimetric assays).

ii) Vision Biosystems (Novocastra) mouse anti-human MCM3 monoclonal antibody (NCL-MCM3) from cell line JCC07 at 1/200 dilution iii) Vision Biosystems (Novocastra) mouse anti-human MCM5 monoclonal antibody (NCL-MCM5) from cell line CRCT5.1 at 1/20 dilution For single antigen stain assays to assess cytoplasmic antigens (PSA), the heat retrieval and secondary staining steps were omitted. For single stain assays to assess nuclear staining antigens (AR, MCM's), the primary staining step was omitted.

It was found that cytoplasmic PSA could be labelled in cultured prostate cells with the D1.12.A3 antibody (FIG. 1a). PSA was also detected with antibodies against 'epitopes' 3 and 4, but not with antibodies against 'epitope' 1 (not shown). Similarly, antibodies to prostate specific acid phosphatase labelled prostate cell cytoplasm, whereas antibodies to prostate specific G-coupled receptor (PSGR) were not effective. In addition, nuclear antigens mini-chromosome maintenance proteins MCM2 and MCM7, and androgen receptor (AR) provided strong labelling, whereas MCM3 and MCM5 were less effective (not shown). When used in combination in dual staining assays, both PSA and MCM5 (FIG. 1b) and PSA and MCM7 (not shown) could label prostate cells and be individually identified due their different cellular locations.

Example 2

Colourimetric labelling of cultured C4-2b prostate cancer cell line with Vector Laboratories ImmPRESS reagents against PSA Androgen receptor (AR) and MCM antigens.

Slides were prepared as described in example 1 using a Thinprep T2000 instrument. All labelling and washing steps were performed manually. The slides were first immersed in 50% methanol for 5 min, and 200 µl DAKO dual endogenous enzyme block (product code (K5361) added for 5 min. The slides were then rinsed 3 times with distilled water and 5 times with DAKO wash buffer (S3006). Ready-to-use ImmPRESS normal horse serum (NHS) at 2.5% was applied to the slides for 20 min to block, followed by 200 µl DAKO A0562 rabbit anti-human PSA polyclonal antibody (or control rabbit antibody) at 0.3 µg/ml and incubated for 10 min. All incubation steps were carried out at room temperature unless otherwise stated. Slides were rinsed 5 times with DAKO wash buffer and 200 µl ImmPRESS Reagent (universal HRP labelled anti-rabbit and anti-mouse) added for 30 min. Slides were rinsed 5 times with DAKO wash buffer and 200 µl ImmPRESS substrate added for 5 min. Substrate used was any one of Vector VIP (SK-4600, purple), DAB (SK-4100, brown), DAB-Ni (SK-4100, grey/black) or Vector NovaRED (SK-4800, red). Slides were washed 5 times with wash buffer.

A heat retrieval step was performed next in order to make the MCM antigens accessible to antibody:—

Slides were immersed 1 mM EDTA heat retrieval buffer, pH7.8 (DAKO) and micro-waved on full power (800 W, 10 min.). Heat retrieval buffer was replenished, and microwaving repeated for 10 min. Slides were prepared in this way in batches of 10. Where a smaller number of samples were being prepared, blank slides were included to bring the total number to 10 for consistency of heat treatment. Slides were allowed to cool for 5 min.

Slides were blocked again for 20 min with 2.5% normal horse serum. The $2^{nd}$ primary antibody, mouse anti-MCM2 D1.12A3 (MRC, Cambridge, UK) or control mouse antibody was added (200 µl at 1 µg/ml) and incubated for 10 min. They were rinsed 5 times with wash buffer, and 200 µl ImmPRESS Reagent (as above) added for 30 min. After five further rinses with wash buffer, 200 µl ImmPRESS substrate was added for 5 min. Substrate was any one of the four listed above, but not the same one as used in the earlier step.

After staining, slides were rinsed with distilled water and immersed in $CuSO_4$ solution (10 g $CuSO_4$, 17 g NaCl in 2 L water) for 5 min, then rinsed again with water. They were then counterstained with either Haematoxylin or Methyl green for 10 seconds and rinsed with water. Finally slides were immersed in xylene for 5 min, air dried and coverslipped ready for analysis.

Antibodies were diluted from stock solutions in DAKO antibody diluent (S0809 or S2022) with diluted 2.5% NHS to desired concentration. Slides were visualised under white light using a Zeiss AxioSKOP 40 microscope fitted with a Prog Res C14 colour camera.

For single stain assays to assess nuclear staining antigens (AR, MCM's), the primary staining step was omitted. For single antigen stain assays to assess cytoplasmic antigens (PSA), the heat retrieval and secondary staining steps were omitted.

In alternative assay formats, the DAKO rabbit anti-PSA polyclonal antibody A0562 at 0.3 µg/ml was substituted with the Insight Biotechnology N-20 rabbit anti-androgen receptor N-terminus specific polyclonal antibody (sc816) at 0.3 µg/ml or anti-androgen receptor C-terminal specific polyclonal antibody (sc815) at 0.3 µg/ml. The D1.12A3 mouse anti-human MCM2 monoclonal antibody at 1.0 µg/ml was replaced with the Santacruz 141.2 mouse anti-MCM7 monoclonal antibody sc-9966 at 3.0 µg/ml. Staining was achieved variously using the following ImmPRESS substrates:— DAB (brown), DAB-Ni (grey.black), novaRED (red), or VIP (purple), either singly or in combination, and with or without counterstain.

Figure 2:
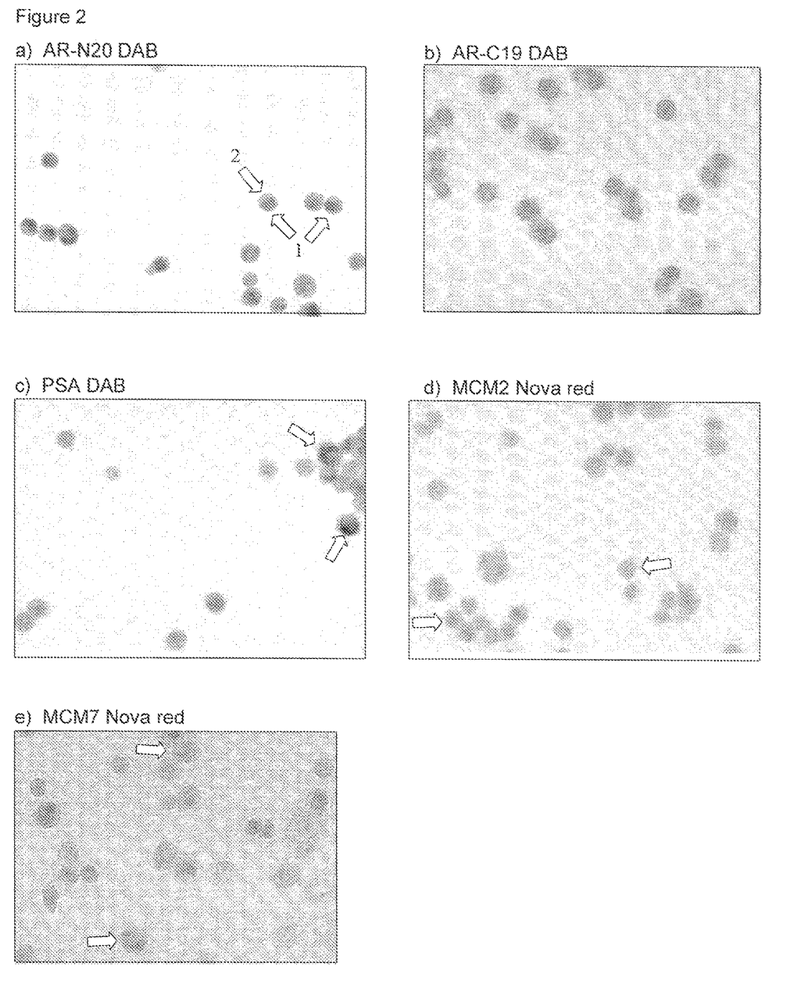
FIG. 2: Colourimetric single-staining of C4-2b cell line with Vector Stain ImmPRESS reagents. Plates are labelled as follows:—a) DAB staining of nucleus only (1) with N-terminal specific anti-AR antibody, with counter-stained cytoplasm (2); b) nonlocalised DAB staining of cells with C-terminal specific anti-AR antibody; c) DAB staining of cytoplasm (arrows) with anti-PSA antibody; d) novaRED staining of nucleus (arrows) with anti-MCM2 antibody; and e) novaRED staining of nucleus (arrows) with anti-MCM2 antibody.
Figure 3:
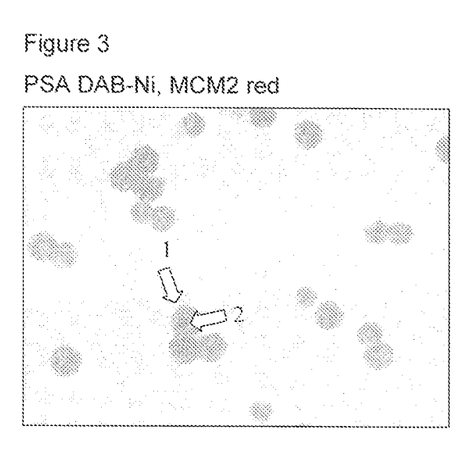
FIG. 3: Colourimetric dual-staining of C4-2b cell line with Vector Stain ImmPRESS reagents. Plate shows DAB-Ni (grey) labelled anti-PSA cytoplasm (1) with novaRED anti-MCM2 antibody labelled nucleus (2).
Figure 4:
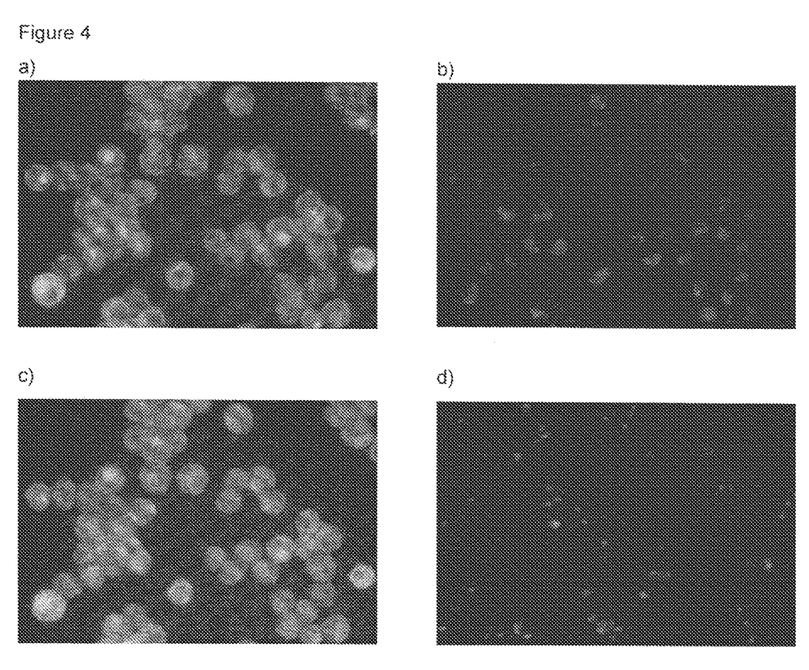
FIG. 4: Fluorescent (Alexafluor) staining of cultured C4-2b prostate cancer cell line. Plate a) with anti-PSA antibody (cytoplasmic); b) anti-MCM7 (nuclear); c) merged, showing distinct separate staining of the two cellular locations and d) merged image using anti-PSA (cytoplasmic) and anti-MCM2 (nuclear) antibodies showing separate localisation.
Figure 5:
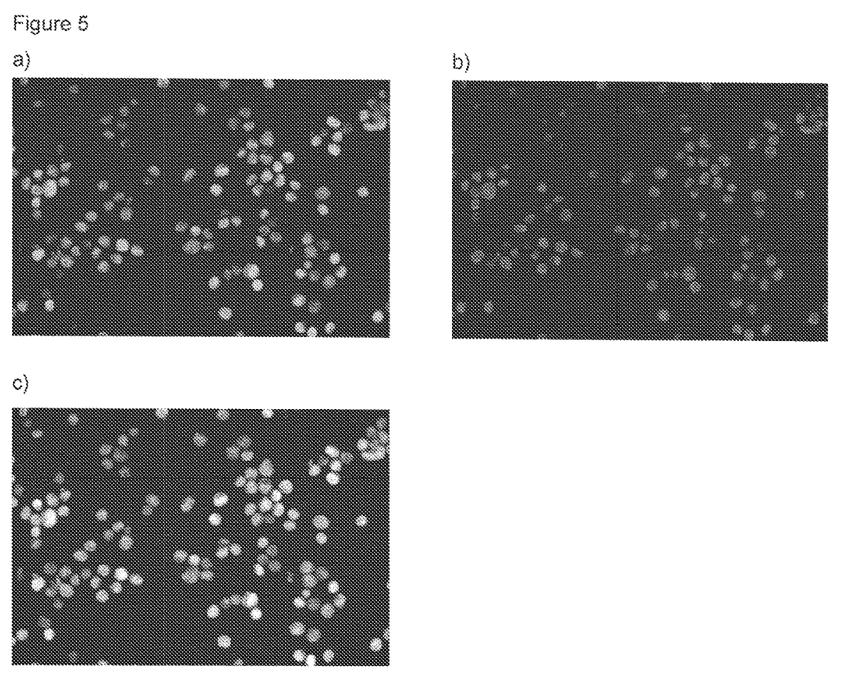
FIG. 5: Fluorescent (Alexafluor) staining of cultured C4-2b prostate cancer cell line. Plate a) with anti-AR antibody (nuclear); b) anti-MCM7 (nuclear); and c) merged, showing nuclear co-localisation of AR and MCM7 antigens.

It was found that, while the AR antibody specific for the N-terminus was able to clearly label the nucleus (FIG. 2a), a C-terminus specific antibody did not show any clear cellular localisation and is therefore not suitable (FIG. 2b). The PSA antigen was also detected in the cytoplasm of cells (FIG. 2c). Antibodies against the cell cycle antigens MCM2 and MCM7 were both able to label the nuclei (FIGS. 2d and e). All of the different substrates were found be effective when used for single staining (not shown). For dual staining, some combinations were less suitable than others due to their similar appearance. DAB-Ni with novaRED and DAB with vecta VIP were found to produce good images (FIG. 3). In this assay format, PSA must be used as a prostate cell-specific marker in combination with one or more MCM antigens. Due to it's nuclear localisation, AR is not suitable in this format.

Example 3

Fluorescent labelling of prostatic cell line C4-2b.

Prostatic cancer cell line C4-2b was cultured and 'Thinprep' slides prepared as detailed in example 1 above.

Cell Staining:

Slides were immersed in 50% methanol for 5 min, washed in distilled water for 5 min and rinsed once with DAKO wash buffer. Two hundred microliters 0.1% Triton X-100 was applied to the slide for 5 min in order to permeabilise the cells. They were then rinsed 3 times with wash buffer and once with water. One hundred microliters of Image-IT FX signal enhancer (Invitrogen 136933) was applied and incubated at room temperature for 30 min. Slides were rinsed 3 times with wash buffer followed by one rinse with distilled water.

Primary antibody mix or control antibody (rabbit anti-PSA at 0.3 µg/ml and mouse anti-MCM2 at 1 µg/ml) was applied to the slides (100 µl each) and incubated for 90 min. Mixes comprised one of the following combinations: i) DAKO rabbit anti-PSA polyclonal antibody A0562 (0.3 µg/ml) and mouse anti-MCM2 D1.12A3 (1.0 µg/ml); ii) DAKO rabbit anti-PSA polyclonal antibody A0562 and Santacruz 141.2 mouse anti-MCM7 monoclonal antibody sc-9966 (1.0 µg/ml); iii) Insight Biotechnology N-20 rabbit anti-androgen receptor N-terminus specific polyclonal antibody sc816 (0.3 µg/ml) and mouse anti-MCM2 D1.12A3; or iv) Insight Biotechnology N-20 rabbit anti-androgen receptor N-terminus specific polyclonal antibody sc816 and Santacruz 141.2 mouse anti-MCM7 monoclonal antibody sc-9966.

Slides were rinsed 3 times with wash buffer and once with water. A 200 µl mix of two Alexafluor secondary antibodies (1/1000 dilution) were applied to slides and incubated for 30 min. The mixes used were as follows, and in relation to the primary antibody mixes described above: i) and iii) Alexafluor 488 (green) anti-rabbit antibody (Invitrogen A11034) and Alexafluor 594 (red) anti-mouse IgG2b antibody (Invitrogen A21145); ii) and iv) Alexafluor 488 (green) anti-rabbit antibody (Invitrogen A11034) and Alexafluor 594 (red) anti-mouse IgG1 antibody (Invitrogen A21125).

Example 4

Fluorescent labelling of prostate cells from patient urine.

Urine samples were provided from two patients with confirmed prostatic cancer, and were processed as follows immediately. Samples were centrifuged in 50 ml falcon tubes at 600 g for 5 min to pellet cells, and the supernatant disposed of. The cell pellet was resuspended in a small volume of Cytolyt (Cytyc Corp) by gentle agitation and the tube topped up 30 ml with CytoLyt. The suspension was vortexed for 5 min and re-centrifuged. The cell pellet was resuspended in 100 µl PreservCyt solution, and transferred to a vial containing 20 ml PreservCyt. The vial was placed in the Thinprep T2000 and slides prepared as described in Example 3 above.

Figure 6:
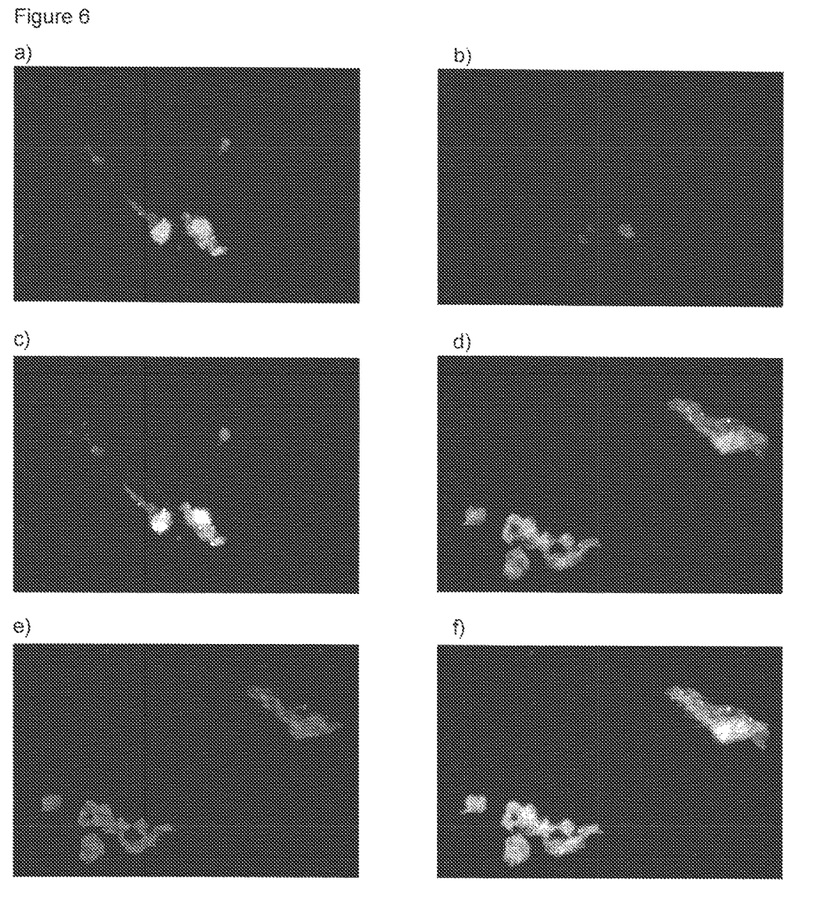
FIG. 6: Dual fluorescent staining of C4-2b prostate cancer cells isolated from a clinical urine sample from patients with confirmed prostatic cancer, with anti-AR and anti-MCM7 antibodies.

Cells were labelled with Santacruz 141.2 mouse anti-MCM7 monoclonal antibody sc-9966 at 1.0 µg/ml and either DAKO rabbit anti-PSA polyclonal antibody A0562 at 0.3 µg/ml or Insight Biotechnology N-20 rabbit anti-androgen receptor N-terminus specific polyclonal antibody (sc816) at 0.3 µg/ml (FIG. 6). Prostate cells were identified in both samples. They were all of irregular morphology, and exhibited varying degrees of cytoplasmic staining due to the poor condition of the cells after prolonged exposure to urine.

Example 5

Effect of removal of debris from urine samples.

Urine samples were centrifuged at 600 g for 10 min to pellet cells. Cells were re-suspended in 1 ml PBS. Total cell counts were determined using a haemocytometer. The volume of cell suspension was adjusted such that 100 µl contained $5\times10^6$ cells (either by addition of PBS, or re-pelleting and re-suspending in an appropriate volume PBS).

Figure 7:
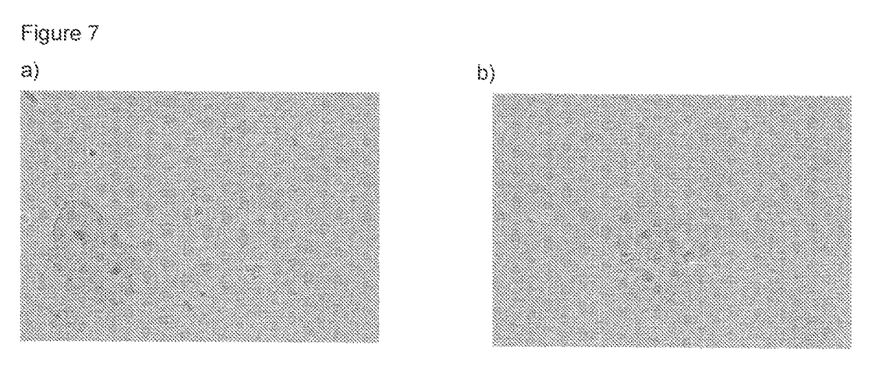
FIG. 7: Removal of injured cells and cellular debris. Haemotoxylin stained bladder endothelial cells isolated from urine samples a) without pre-treatment with Immunosolv DeadCert particles and b) after treatment to remove dead or dying cells and other cellular debris.

A stock vial of Immunosolv Dead Cert nanoparticles (Imunosolv Ltd., Edinburgh, UK) was vortexed for 30 s. Twenty five microliters of nanoparticles were transferred to an Eppendorf tube containing 1 ml PBS. The tube was placed in the provided magnetic separator for 3-5 min, until particles had collected against the magnet. The buffer was removed by pipetting, and the tube removed. Particles were resuspended in 100 µl PBS by vortexing. One hundred microliters cells ($5\times10^6$ cells) were added to the particle suspension, and the mixture incubated at 4° C. for 40 min. During this incubation, the magnetic nanoparticles bind to antigens selectively expressed on the surface of any dead or dying cells. A further 800 µl PBS was added to the tube and mixed gently, and the tube then placed back into the magnetic separator for 5 min. The supernatant containing viable healthy cells was removed by pipetting, and added to a vial of PreservCyt (20 ml). A second 100 µl aliquot of cells that had not been pre-depleted with DeadCert particles was added to another vial of PreservCyte. Both samples were then processed in a Thinprep T200 as described in example 1. Slides were stained with haemotoxylin for visualisation FIG. 7.

There were large numbers of particles of debris arising primarily from non-viable cells in the untreated samples. These can often be non-specifically labelled, and are often not distinguishable from genuine cancer cells due to the variable cellular morphology of the latter that is frequently seen. In contrast, treated samples contain far fewer particles of debris, enabling a more accurate and robust assessment of the patient to be made.

Example 6

Survival of prostatic cancer cells in urine.

Figure 8:
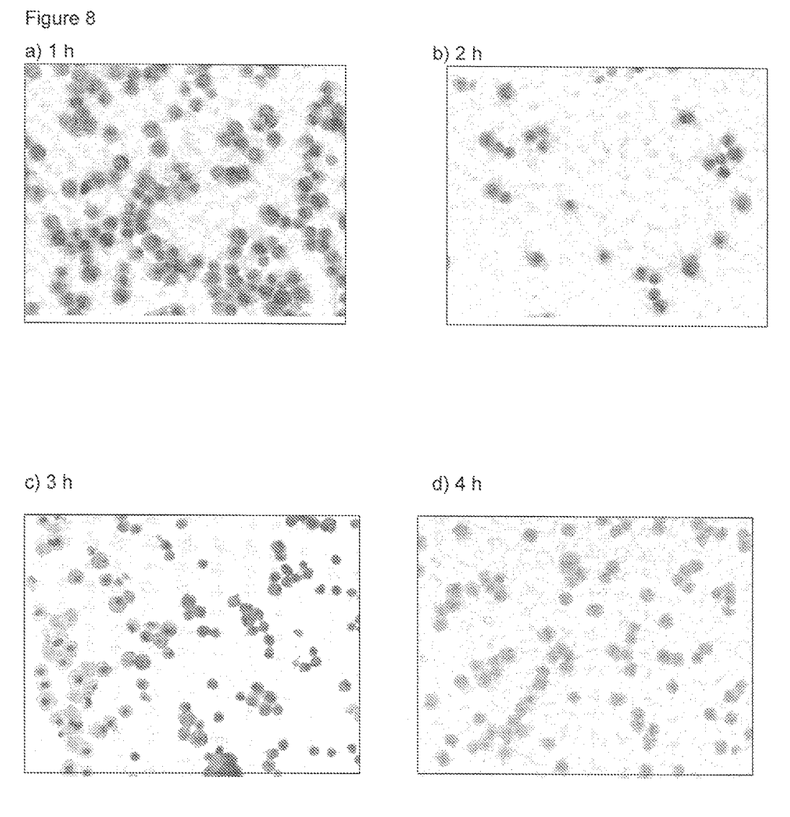
FIG. 8: Survival/health of cultured prostatic C4-2b cell nuclei in urine over 8a-1 hour, 8b-2 hours, 8c-3 hours, and 8d-4 hours. Clear nuclear staining indicates that cells are in good condition. Less intense staining, lack of staining, and increasing cytoplasmic staining indicate that cells are losing viability and would not be clearly identified as prostate cancer cells in patient samples.

Prostatic cell line C4-2b was cultured as described in example 1. When culture flasks had reached 80% confluence, cells were harvested by centrifugation, resuspended in PBS (phosphate-buffered saline) and counted. Approximately $2\times10^7$ cells in 5 ml PBS were added to 25 ml urine provided by healthy donors and stored at 4° C. The samples were removed from the fridge after 1 h, 2 h, 3 h, and 4 h and slides prepared as detailed in example 1 using a Thinprep T2000 instrument. The slides were stained using mouse anti-MCM2 D1.12A3 antibody and DAKO anti-mouse alkaline phosphatase reagents as in example 1, and viewed under both white light (FIG. 8). At 1 h and 2 h the cells showed clear nuclear staining of strong intensity. By 3 h staining was less clearly nuclear and less intense. At this point some cells did not stain positive for MCM. By 4 h the proportion of healthy cells had reduced significantly (data not shown).

It is of particular importance that cells stained with MCM indicated that nuclear integrity remained high to 4 hours with a gradual deterioration to 72 hours thereafter (data not shown). It was shown that the disappearance/dissolution of the protective cell membrane began from 1 hour onward in which PSA, as an index of cellular integrity staining the cytoplasm of prostate specific cells, deteriorated sharply from 1 hour onwards (data not shown).

Example 7

Staining of Prostate Cancer cell line with Androgen Receptor (AR) and Mini Chromosome Maintenance Protein (MCM) antibodies Early studies on patients with prostate cancer indicated that prostate epithelial cells could be captured in the urine of patients presenting with high serum prostate specific antigen (PSA) values. The cells were few in number and had to be processed within one hour of void. We have already established a method for prostate cell detection in urine using MCM as a nuclear marker and PSA as a cytoplasmic marker. The rapid deterioration of these cells in urine, however, particularly the cell membrane and hence the cytoplasm of the cell required a more robust antibody marker.

It was noted that the nucleus of the prostate epithelial cell remained intact for up to 4 hours post void (see Example 6). A nuclear marker with specific affinity to prostate tissue was selected and investigated. Good definition of prostate cells was achieved using androgen receptor antibodies using both prostate cancer cell lines and in the urines of patients with prostate cancer or those with high serum PSA values.

Figure 9:
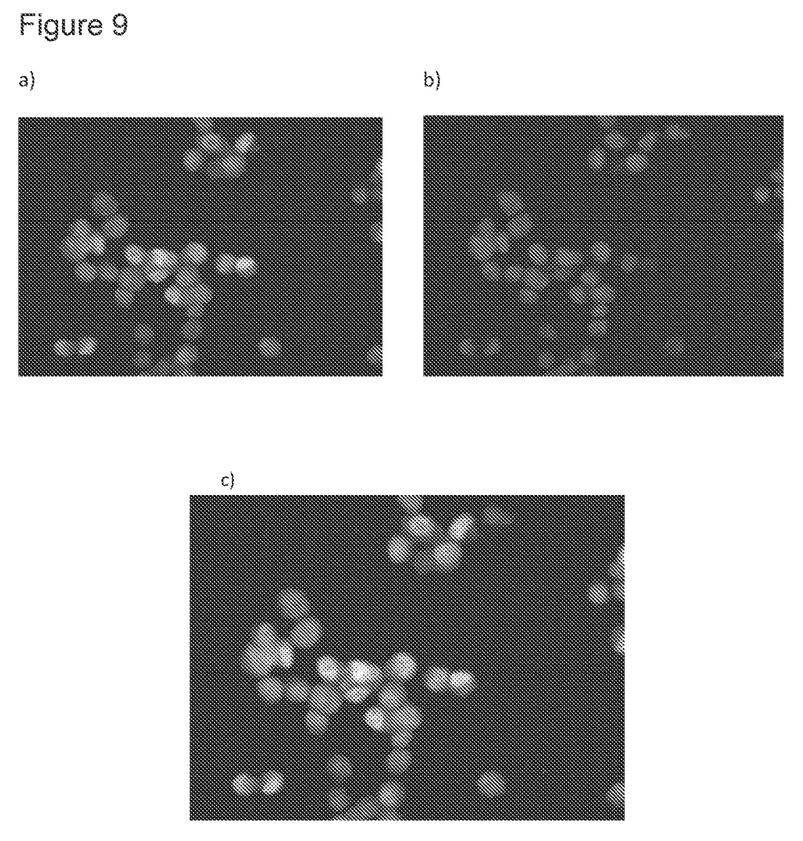
FIG. 9: Dual fluorescent staining of prostate cancer cells isolated from a clinical urine sample from patients with confirmed prostatic cancer, with (a) anti-AR (green) and (b) anti-MCM7 (red) antibodies and (c) Merged image of a double staining with AR and MCM.

Normal urines spiked with an established prostate cancer cell line (C42b) were prepared in the laboratory using urocyte slides on an Hologic T2000 machine. The slides were immersed for 5 minutes in 50% methanol, washed with deionised water and 200 ul 0.2% Triton X-100 added for 5 minutes to permeabilise the cells. A further rinse×3 with DAKO buffer and ×1 with deionised water is followed with 2 drops (100 ul) Image-IT Fx signal enhancer or sufficient volume to cover each coverslip or section and then incubated for 30 minutes at room temperature. A further rinse ×3 with buffer and ×1 with water is followed by incubation with 200 ul of primary antibodies AR (0.3 ug/ml AR-N20 sourced from Santa Cruz catalogue no sc-816) and 1.15 ug/ml MCM (MCM7 sourced from Santa Cruz catalogue no sc9966) in 0.5% milk powder for 60 minutes. The slides are rinsed ×3 with buffer and ×1 with deionised water, and then incubated with the relevant secondary Alexafluor antibodies (alexafluor 488 goat anti-rabbit IgG (H+L; Invitrogen cat no A-11034, and Alexafluor 594 goat anti-mouse IgG1 (γ1); Invitrogen cat no A-21125) in the dark for 30 minutes. The slides are again rinsed ×3 with buffer and ×1 with water, prior to the application of 1 drop of Prolong Gold Anti-fade reagent at room temperature followed by coverslipping of all slides. The slides are cured by placing the mounted sample on a flat dry surface and incubating at room temperature in the dark for 24 hours. Fluorescence was detected using a fluorescent microscope with different fluorescence filters at 10 seconds (FIG. 9).

The experiment showed a clear and defined nuclear staining both for Androgen Receptor and Mini Chromosome Maintenance Protein.

An identical experiment was performed using MCM7 (at 1:100 dilution) and a rabbit monoclonal androgen receptor antibody (AR) (sourced from Epitomics Inc.). Moreover another experiment was performed using MCM2 at a 1:50 dilution and a rabbit monoclonal androgen receptor antibody (AR) (sourced from Epitomics Inc.). Slides were stained in two different combinations using a mixed population of C42b prostate epithelial cells and EJ28 bladder cancer cells as the negative control for evaluation of the specificity and fixation of prostate nuclei by the MCM2 or MCM7 and androgen receptor combination. The methodology adopted was identical to that used in the C42b cell line incorporating the androgen receptor polyclonal antibody (above) and MCM7. In this experiment the C42b cells were stained with MCM2 at 1:50 dilution and RabMAb AR at 1:100 dilution. The individual nuclear staining components were clearly identified under fluorescent microscopy using AF488-1/1000 with the androgen receptor at 1:100 dilution and AF594-1/1000 in combination with MCM2 at 1:50 dilution (data not shown). Individual images of prostate cell lines stained in these circumstances showed clear identification of staining properties in the nuclei of the identified prostate cells. When the androgen receptor and MCM2 antibodies combined with the relevant Alexafluor fluorescent antibody were combined there was good evidence of a clear and defined nuclear staining pattern whereby the green colouration of the androgen receptor together with the red colour of the MCM2 nuclear stain produced an orange coloured combination identifying prostate epithelial cells from a standardised prostate malignant cell line with dual nuclear staining characteristics (data not shown). Further work using both mixed populations of C42b and EJ28 prostate and bladder malignant cell lines respectively, when combined with androgen receptor and MCM7 showed good evidence of prostate cells with a stained yellow nucleus. EJ28 bladder cancer cells were not stained at all. Likewise, a mixed population of C42b and EJ28 cell lines when stained with androgen receptor at 1:100 and MCM2 at 1:50 dilutions showed a merged image of mixed populations C42b and EJ28 stained cells in which EJ28 stained cells showed no evidence of androgen receptor stain.

These experiments confirm that there was clear and defined nuclear staining with combinations of MAb AR plus MCM7 and likewise staining activity for MAb AR and MCM2. These data confirm that epithelial prostate cancer cell lines can be stained at a nuclear level using both MCM2 and MCM7 in association with an androgen receptor antibody, in this case MAb AR.

What is claimed is:

1. A diagnostic or prognostic assay for the detection of prostate cancer cells in a urine sample, the assay comprising the steps of:
   i) obtaining an isolated cell sample from said urine sample and contacting the isolated cell sample with a binding agent that specifically binds a minichromosome maintenance (MCM) polypeptide;
   ii) contacting the isolated cell sample with a further binding agent that specifically binds an androgen receptor polypeptide [AR];
   iii) contacting the isolated cell sample with a still further binding agent that specifically binds prostate specific antigen [PSA];
   iv) detecting the binding of two or more of the binding agents having different specificities; and
   v) determining the number of cells in said isolated cell sample that positively bind the two or more binding agents, wherein the number of positive cells is an indicator of the presence of prostate cancer cells in the urine sample;
   wherein the binding agents are antibodies.

2. An assay according to claim 1, wherein said MCM polypeptide is selected from the group consisting of: MCM2, MCM3, MCM4, MCM5, MCM6 or an MCM7 polypeptide.

3. An assay according to claim 2, wherein said MCM polypeptide is selected from MCM2 and MCM7.

4. An assay according to claim 2, wherein said MCM polypeptide is MCM2.

5. An assay according to claim 2, wherein said MCM polypeptide is MCM7.

6. An assay according to claim 1, wherein said assay detects at least one polypeptide selected from AR and PSA.

7. An assay according to claim 6, wherein said assay detects AR, PSA, and a MCM polypeptide selected from MCM2 and MCM7.

8. An assay according to claim 1, wherein step (iii) comes before step (ii).

9. An assay according to claim 1, wherein said binding agent is a monoclonal antibody, or active binding fragment thereof.

10. An assay according to claim 1, wherein said urine sample is filtered, and wherein said filtered sample provides said isolated cell sample.

11. A diagnostic or prognostic assay for the determination of prostate cancer in a subject comprising the steps:
   i) obtaining a serum sample from the subject and contacting the sample with a binding agent that specifically binds PSA;
   ii) detecting the presence of PSA in said serum sample;
   iii) obtaining a urine sample from the subject, preparing an isolated cell sample and contacting said cell sample with first binding agent that specifically binds a MCM polypeptide and a second binding agent that specifically binds to an androgen receptor polypeptide;
   iv) detecting the presence of said MCM polypeptide and androgen receptor; and
   v) determining the number of cells in said isolated cell sample that positively bind both MCM and androgen receptor, wherein the number of positive cells is an indicator of the presence of prostate cancer cells;
   wherein the binding agents are antibodies.

12. An assay according to claim 11, wherein said MCM polypeptide is selected from MCM2 and MCM7.

13. An assay according to claim 12, wherein said MCM polypeptide is MCM2.

14. An assay according to claim 12, wherein said MCM polypeptide is MCM7.

15. An assay according to claim 1, wherein said detection of binding agents is by fluorescence emission.

16. An assay according to claim 1, wherein said detection of binding agents is by enzymic means.

* * * * *